United States Patent
Andrews et al.

(10) Patent No.: US 8,609,165 B1
(45) Date of Patent: Dec. 17, 2013

(54) DIETARY SUPPLEMENT FOR OPTIMIZING GLUCOSE LEVELS, INCREASING ENERGY, AND IMPROVING GENERAL HEALTH

(75) Inventors: Kevin M. Andrews, Apalachin, NY (US); Randall P. Wight, Martinez, CA (US)

(73) Assignee: E5 LLC, Honolulu, HI (US)

( * ) Notice: Subject to any disclaimer, the term of this patent is extended or adjusted under 35 U.S.C. 154(b) by 0 days.

(21) Appl. No.: 12/803,737

(22) Filed: Jul. 2, 2010

Related U.S. Application Data

(60) Provisional application No. 61/270,030, filed on Jul. 2, 2009.

(51) Int. Cl.
| | |
|---|---|
| A23L 1/30 | (2006.01) |
| A01N 37/12 | (2006.01) |
| A01N 37/44 | (2006.01) |
| A61K 38/43 | (2006.01) |
| A23L 1/302 | (2006.01) |
| A23L 1/29 | (2006.01) |
| A61K 31/195 | (2006.01) |
| A61K 31/198 | (2006.01) |

(52) U.S. Cl.
CPC ............... *A23L 1/302* (2013.01); *A23L 1/296* (2013.01); *A61K 31/195* (2013.01); *A61K 31/198* (2013.01)
USPC ............... 426/74; 426/72; 514/561; 514/562; 424/94.1

(58) Field of Classification Search
USPC ............... 426/74; 514/561, 562; 424/94.1
See application file for complete search history.

(56) References Cited

U.S. PATENT DOCUMENTS

| | | | |
|---|---|---|---|
| 2002/0061870 A1 * | 5/2002 | Pearson et al. | 514/184 |
| 2005/0256178 A1 * | 11/2005 | Eggersdorfer et al. | 514/393 |
| 2008/0268066 A1 * | 10/2008 | Yie et al. | 424/641 |

* cited by examiner

*Primary Examiner* — Rena Dye
*Assistant Examiner* — Assaf Zilbering
(74) *Attorney, Agent, or Firm* — James Creighton Wray

(57) ABSTRACT

A dietary supplement can optimize glucose levels, increase energy, and provide other health benefits including combinations of alpha lipoic acid, vanadium, zinc, vitamin C and biotin.

15 Claims, No Drawings

DIETARY SUPPLEMENT FOR OPTIMIZING GLUCOSE LEVELS, INCREASING ENERGY, AND IMPROVING GENERAL HEALTH

This application claims the benefit of U.S. Provisional Application No. 61/270,030, filed Jul. 2, 2009, which is hereby incorporated by reference in its entirety.

DESCRIPTION OF THE INVENTION

A novel dietary supplement composition is provided that can optimize glucose levels, increase energy and provide improvements in diabetes, diabetic neuropathy, age related conditions, chronic fatigue syndrome, hepatitis, cataracts, brain function, skin, teeth, bones and other general health benefits. Described also is a method for achieving said benefits with said composition. Further described is an additional method for manufacturing such composition to achieve controlled uptake of the said composition in the subject's blood plasma to lengthen the biological benefit of each dose. An embodiment of said composition includes alpha lipoic acid, vanadium, zinc, vitamin C and biotin.

The present invention provides a dietary supplement that can optimize glucose levels, increase energy, and provide other health benefits. The invention includes combinations of components in effective amounts of alpha lipoic acid and vanadium.

The new dietary supplement that includes the following components per daily dose:
    about 50 mg to 1000 mg of alpha lipoic acid; and
    about 1 mcg to 100 mg of vanadium;

The dietary supplement of the invention that can optimize glucose levels, increase energy, and provide other health benefits by ingestion of a combination components in effective amounts of alpha lipoic acid and Sc.

The invention also provides a dietary supplement including the following components per daily dose:
    about 50 mg to 1000 mg of alpha lipoic acid,
    about 1 mg to 100 mg of zinc.

A dietary supplement of the invention includes the following components per daily dose:
    about 50 mg to 1000 mg of alpha lipoic acid,
    about 1 mcg to 100 mg of vanadium, and
    about 1 mg to 100 mg of zinc.

One dietary supplement provided by the invention includes the following components per daily dose:
    about 50 mg to 1000 mg of alpha lipoic acid,
    about 1 mcg to 20 mg of vanadium,
    about 1 mg to 100 mg of zinc, and
    about 1 mg to 1000 mg of vitamin C;

A dietary supplement of the invention that includes the following components per daily dose:
    about 50 mg to 1000 mg of alpha lipoic acid,
    about 1 mcg to 100 mg of vanadium,
    about 1 mg to 100 mg of zinc,
    about 1 mg to 1000 mg of vitamin C, and
    about 1 mg to 1000 mg of biotin;

One embodiment of the invention contains:
    400 mg of alpha lipoic acid,
    60 mcg of vanadium,
    5 mg of zinc,
    60 mg of vitamin C, and
    100 mg of biotin.

Another embodiment of the invention contains:
    400 mg of alpha lipoic acid,
    60 mcg of vanadium,
    5 mg of zinc, and
    60 mg of vitamin C;

One embodiment of this invention contains 400 mg of alpha lipoic acid, 60 mcg of vanadium, 5 mg of zinc, 60 mg of vitamin C, and optionally 100 mg of biotin as a recommended daily dose. The formulae are manufactured in a tablet or caplet form incorporating tightly packed finely divided elements and fillers to achieve a controlled uptake in a digestive system that optimizes blood plasma level for a duration that optimizes efficacy of the compositions. A target controlled uptake of 3-6 hours would be desirable depending on the individual and their particular physical conditions.

The invention provides a method of optimizing glucose levels, increasing energy and providing improvements in diabetes, diabetic neuropathy, age related conditions, chronic fatigue syndrome, hepatitis, cataracts, brain function, skin, teeth, bones and other general health benefits by administering the composition in any of the above-described compositions on a regular basis.

The invention provides a method of optimizing glucose levels, increasing energy and providing improvements in diabetes, diabetic neuropathy, age related conditions, chronic fatigue syndrome, hepatitis, cataracts, brain function, skin, teeth, bones and other general health benefits by administering the composition on a daily basis.

The invention also includes a method of providing the new method of manufacturing the compositions in claims 1-9 in a tablet or caplet form to achieve an uptake rate that optimizes blood plasma level of the compositions and their effective metabolytes for a duration that optimizes efficacy of the new product.

A method of administering manufacturing the compositions in a tablet or caplet form is provided wherein a first fraction of the active composition is composed to achieve quick uptake in the gastrointestinal tract, and a second fraction is composed with suitable packing and fillers to achieve slow uptake in the gastrointestinal tract. The new rapidly gastrointestinally dissolving outer layer initially increases blood plasma levels of the active ingredients and their metabolytes to an optimal peak and then the slower dissolving of the remainder sustains the peak.

The present invention relates generally to dietary supplements, and, more particularly, to a special formulation that optimizes glucose levels, increases energy and provides improvements in diabetes, diabetic neuropathy, age related conditions, chronic fatigue syndrome, hepatitis, cataracts, brain function, skin, teeth, bones and other general health benefits. These are serious medical conditions in which poor diet habits, nutritional deficiencies, genetics, and lack of exercise all play a role.

Alpha lipoic acid is known to be a powerful and versatile antioxidant that is both needed by the body and found in every cell, where the alpha lipoic acid is involved in the conversion of glucose into energy. Alpha lipoic acid holds unique properties, as alpha lipoic acid is unlike any other antioxidants which only work in water or fatty tissues but not both, Alpha lipoic acid is both water and fat soluble and can work throughout the entire body as a super antioxidant, destroying free radicals, making alpha lipoic acid a powerful natural weapon for anti-aging regimes. Alpha lipoic acid can have a direct influence on the regeneration of other key antioxidants including glutathione, Vitamin C, Vitamin E, and the uptake of CoQ10 in the cell.

Vanadium is an essential trace mineral. Vanadium is important in the treatment of diabetes. The mineral works by acting like insulin and, thereby helping cells to absorb sugar more effectively. Human studies show that vanadium greatly reduces the needs for insulin and hypoglycemic medications. Vanadium also lowers blood sugar as well. Vanadium sulfate has been found to benefit both Type I and Type II diabetes. In humans Vanadium appears to have the insulin-mimicking effect that Type I diabetics need, as well as the ability to overcome the insulin resistance that defines Type II diabetes.

Zinc, is an essential mineral that is found in every cell in a body. Zinc stimulates the activity of over 100 enzymes. Among its many functions, zinc helps maintain a healthy immune system, is needed for wound heating, helps maintain senses of taste and smell, assists in the breakdown of carbohydrate for energy and is needed for DNA synthesis. Zinc also supports normal growth and development during pregnancy, childhood, and adolescence. Zinc helps sperm develop and is needed for ovulation and fertilization. Zinc is stored in the muscles, blood cells, retinas of the eyes, skin, bone, kidney, liver, pancreas and, in men, the prostate. Zinc is an antioxidant, protecting cells from free radicals. Zinc deficiencies have been noted in people with diabetes, and a direct correlation has been made to cardiovascular disease and diabetes. Low zinc levels and high oxidative stress caused by diabetes or poor glucose metabolism and other illnesses can lead to irreversible cell damage that can increase the negative effects of diabetes, including heart attack and strokes.

Vitamin C is required for the synthesis of collagen, an important structural component of blood vessels, tendons, ligaments, and bone. Vitamin C also plays an important role in the synthesis of the neurotransmitter, norepinephrine. Vitamin C is also a highly effective antioxidant. Even in small amounts, vitamin C can protect indispensable molecules in the body, such as proteins, lipids, carbohydrates, and nucleic acids DNA and RNA from damage by free radicals and reactive oxygen species that can be generated during normal metabolism as well as through exposure to toxins and pollutants. Vitamin C may also be able to regenerate other antioxidants such as vitamin E. Recent studies have shown that low vitamin C levels may increase risks of diabetes, and higher intake of Vitamin C may reduce risks of developing diabetes.

Biotin is necessary for cell growth, production of fatty acids and metabolism of fats and amino acids. Biotin plays a role in the citric acid cycle, which is the process by which biochemical energy is generated during aerobic respiration. Biotin not only assists in various metabolic reactions but also helps to transfer carbon dioxide. Biotin is also helpful in maintaining a steady blood sugar level. Diabetics may also benefit from biotin supplementation. In both insulin-dependent and non-insulin-dependent diabetes, supplementation with biotin can improve blood sugar control and help control fasting blood glucose levels. Biotin can also play a role in preventing the neuropathy often associated with diabetes, reducing both the numbness and tingling associated with poor glucose control.

The present invention provides a novel dietary supplement composition that can optimize glucose levels, increase energy and provide improvements in diabetes, diabetic neuropathy, age related conditions, chronic fatigue syndrome, hepatitis, cataracts, brain function, skin, teeth, bones and other general health benefits.

A method for achieving the benefits controls uptake of the compositions. Providing the compositions in high initial controlled uptake establishes a beneficial level of the composition in blood, plasma, and lowered continued uptake lengthens the biological benefit of each dose. The composition includes alpha lipoic acid, vanadium, zinc, vitamin C and biotin.

Although it is known that the various ingredients may have modest benefits for some of the conditions for which this invention benefits, the unique combination of this invention allows both synergistic benefits not realized in the individual ingredients. The synergistic effects include broader systemic improvement, a multi-prong approach to inherently systemic health issues, and achievement of results at lower doses than possible with the individual ingredients of the composition.

While the invention has been described with reference to specific embodiments, modifications and variations of the invention may be constructed without departing from the scope of the invention, which is defined in the following claims.

We claim:

1. A dietary supplement composition consisting of a combination of effective amounts of alpha lipoic acid, biotin, vitamin C, zinc and vanadium, as active ingredients, and fillers packed in single dose units, having a first fraction and a second fraction of the active ingredients wherein the effective amount of vanadium is about 60 mcg to 100 mg, and wherein the first fraction of the active ingredients rapidly dissolve in a gastrointestinal tract to achieve rapid uptake in the gastrointestinal tract, and the second fraction of the active ingredients is adapted for achieving slow uptake in the gastrointestinal tract, thereby rapidly dissolving the first fraction of the active ingredients for slowly dissolving increasing blood plasma levels of the active ingredients and their metabolytes initially to an optimal peak and then sustaining the optimal peak.

2. The composition of claim 1, wherein the effective range of alpha lipoic acid is about 50 mg to 1000 mg, the effective range of vanadium is about 1 mcg to 100 mg, the effective range of zinc is about 1 mg to 100 mg, the effective range of vitamin C is 1 mg to 1000 mg, the effective range of biotin is 1 mg to 1000 mg.

3. The composition of claim 2 comprising 400 mg of alpha lipoic acid, 60 mcg of vanadium, 5 mg of zinc, 60 mg of vitamin C and 100 mg of biotin.

4. The composition of claim 1, comprising about 50 mg to 1000 mg of alpha lipoic acid and about 60 mcg to 100 mg of vanadium.

5. The composition of claim 1 comprising about 50 mg to 1000 mg of alpha lipoic acid, about 60 mcg to 100 mg of vanadium and about 1 mg to 100 mg zinc.

6. The composition of claim 5 comprising about 400 mg of alpha lipoic acid, about 60 mcg of vanadium, about 5 mg of zinc and about 60 mg of vitamin C.

7. The composition of claim 1, wherein a single dose of the combination is a daily dose.

8. A dietary supplement composition consisting of a combination of effective amounts of alpha lipoic acid, zinc and vanadium as active ingredients and fillers in single dose units, having a first fraction and a second fraction of the active ingredients wherein the first fraction of the active ingredients rapidly dissolve in a gastrointestinal tract to achieve rapid uptake in the gastrointestinal tract, and the second fraction of the active ingredients is adapted for achieving slow uptake in the gastrointestinal tract, thereby rapidly dissolving the first fraction of the active ingredients for slowly dissolving increasing blood plasma levels of the active ingredients and their metabolytes initially to an optimal peak and then sustaining the optimal peak.

9. The composition of claim 8 comprising about 50 mg to 1000 mg of alpha lipoic acid and about 1 mg to 100 mg of zinc.

10. The composition of claim 8 comprising about 50 mg to 1000 mg of alpha lipoic acid, about 1 mg to 100 mg of zinc and about 1 mg to 1000 mg of vitamin C.

11. The composition of claim 8, wherein a single dose of the combination is a daily dose.

12. A method of optimizing glucose levels, increasing energy and providing improvements in diabetes, diabetic neuropathy, age related conditions, chronic fatigue syndrome, hepatitis, cataracts, brain function, skin teeth, bones and other general health benefits by administering said composition in claim 1 on a daily basis said composition consisting of a combination of effective amounts of alpha lipoic acid, biotin, vitamin C, zinc and vanadium, as active ingredients, and fillers packed in single dose units, having a first fraction and a second fraction of the active ingredients wherein the effective amount of vanadium is about 60 mcg to 100 mg, and wherein the first fraction of the active ingredients rapidly dissolve in a gastrointestinal tract to achieve rapid uptake in the gastrointestinal tract, and the second fraction of the active ingredients is adapted for achieving slow uptake in the gastrointestinal tract, thereby rapidly dissolving the first fraction of the active ingredients for slowly dissolving increasing blood plasma levels of the active ingredients and their metabolytes initially to an optimal peak and then sustaining the optimal peak.

13. A method of manufacturing the compositions in claim 1 in a tablet or caplet format incorporating packing and fillers to achieve an uptake rate that optimizes blood plasma level for a duration that optimizes efficacy.

14. A method of manufacturing the compositions in claim 1 in a tablet or caplet format, wherein a first fraction of the active composition is composed with components to achieve rapid uptake in the gastrointestinal tract and a second fraction is composed by suitable packing and fillers thereby achieving slow uptake in the gastrointestinal tract, the method rapidly increasing blood plasma levels of the active ingredients initially to an optimal peak and then sustaining the optimal peak.

15. A dietary supplement composition consisting of a combination of effective amounts of alpha lipoic acid, biotin, vitamin C, zinc and vanadium packed in single dose units.

\* \* \* \* \*